United States Patent [19]
Kanz et al.

[11] Patent Number: 5,866,115
[45] Date of Patent: Feb. 2, 1999

[54] PROCESS FOR PREPARING DENDRITIC CELLS, CELLS THUS PRODUCED AND CONTAINERS FOR CARRYING OUT THIS PROCESS

[75] Inventors: Lothar Kanz, Freiburg; Wolfram Brugger, Kirchzarten; Reinhard Henschler, Freiburg; Gabriele Köhler, Freiburg; Hans-Eckart Schaefer, Freiburg; Albrecht Lindemann, Sölden; Roland Mertelsmann, Freiburg; Andreas Mackensen, Freiburg; Paul Fisch, Freiburg; Birgit Herbst, Schallstadt, all of Germany

[73] Assignee: Klinikum Der Albert-Ludwigs-Universitat Freiburg, Freiburg, Germany

[21] Appl. No.: 727,495

[22] PCT Filed: Apr. 11, 1995

[86] PCT No.: PCT/DE95/00512

§ 371 Date: Oct. 11, 1996

§ 102(e) Date: Oct. 11, 1996

[87] PCT Pub. No.: WO95/28479

PCT Pub. Date: Oct. 26, 1995

[30] Foreign Application Priority Data

Apr. 14, 1994 [DE] Germany .......................... 44 12 794.4

[51] Int. Cl.⁶ .......................... A61K 35/00; A61K 35/10; C12N 15/85
[52] U.S. Cl. ....................... 424/93.7; 424/85.2; 424/85.7; 514/825; 435/325
[58] Field of Search ................................ 424/85.2, 85.7, 424/93.7, 325; 514/825

[56] References Cited

FOREIGN PATENT DOCUMENTS

| 9320185 | 10/1993 | WIPO . |
| 9320186 | 10/1993 | WIPO . |
| 9321936 | 11/1993 | WIPO . |
| 9403587 | 2/1994 | WIPO . |

OTHER PUBLICATIONS

Osband, ME et al. 1990, Immunol. Today 11:193–195.
Brugger, W. et al. 1993. Blood, 81(10):2579–2584.
Ferrajoli, A et al. 1993. Ann. Hematol. 67(6):271–284.
Dercksen, MW. et al. 1993. Int. J. Cancer, 68(5):996–1003.
Ex Vivo Expansion of Enriched Peripheral Blood CD34+ Progenitor Cells By Stem Cell Factor, Interleukin–1Beta (IL–1 Beta), IL–6, IL–3, Interferon–Gamma, and Erythropoietin, Blood, vol. 81, No. 10, pp. 2579–2584 (1993), Brugger et al.
Human Stem Cell Factor (SCF) Promotes the Growth of Dendritic Langerhans Cells from their Primitive Porgenitors (CFU–DL) In Human Bone Marrow, Blood (Supplement 1), vol. 82, No. 10, p. 102a (1993), Saraya et al.
Growth Factors Controlling Interleukin–4 Action on Hematopoietic Progenitors, Database Medline, US National Library of Medicine (NLM), Ann Hematology pp. 277–284 (1993), Ferrajoli et al.
Ex Vivo Generation of Functionally Active Antigen Presenting Cells From Peripheral blood (CD34+ Hematopoietic Progenitor Cells in Cancer Patients, Blood (Supplement 1), vol. 84, No. 10, p. 228a )1994), Fisch, P. et al.

*Primary Examiner*—Lila Feisee
*Assistant Examiner*—Geetha P. Bansal
*Attorney, Agent, or Firm*—Fulbright & Jaworski,, LLP.

[57] ABSTRACT

Dendritic cells are of interest therapeutically as antigen-presenting cells. A process is disclosed in which peripheral blood cells are first isolated and the CD 34 antigen-expressing blood progenitor cells which they contain are then enriched. These enriched cells are expanded ex-vivo using a combination of haematopoietic growth factors and cytokines. Over a period of 10–20 days, they give rise, in particular to dendritic cells which, where appropriate, can be purified still further. These cells are functionally active with regard to the ability to present antigen.

18 Claims, 1 Drawing Sheet

PROCESS FOR PREPARING DENDRITIC CELLS, CELLS THUS PRODUCED AND CONTAINERS FOR CARRYING OUT THIS PROCESS

The present invention relates to the preparation of dendritic cells, which can not only be of use in basic research but can also advantageously be used therapeutically.

EPA 92.400879.0 discloses a process for producing human dendritic cells. In this, process, CD 34$^+$ cells are treated with tumour necrosis factor-α (TNF-α) and either interleukin-3 or GM-CSF. However, it has emerged that the desired cells cannot be obtained in the requisite yield and purity when using this process.

Dendritic cells constitute the most potent antigen-presenting cells in the organism. They are derived from bone marrow progenitor cells, circulate in small numbers in the peripheral blood and appear as so-called Langerhans' cells or terminally differentiated cells (dendritic cells) in the epidermis of the skin, the gastrointestinal mucosa, the visceral pleura or the epithelia of the urogenital tract.

Following exposure to antigen, these cells migrate from the skin into the paracortex of draining lymph nodes, where, as terminally differentiated cells, they elicit a specific T cell response. Their function as antigen-presenting cells can be demonstrated in vitro in the autologous and allogenic "mixed lymphocyte reaction" and in test systems to which soluble antigens are added.

The dendritic cells can be differentiated from monocytes/macrophages, which likewise constitute antigen-presenting cells but express other surface markers. A particular differentiating marker is the CD 14 antigen, which is not found in dendritic cells but is possessed by monocytes and macrophages. The dendritic cells are not phagocytic, in contrast to the monocytes/macrophages, which are strongly phagocytosing cells. The surface antigens in the circulating dendritic cells can be defined as follows: CD1a$^+$, CD1c$^+$, CD 13$^+$, CD 33$^+$, CD 14$^-$ CD 16$^-$, CD 3$^-$, CD 19$^-$ and MHC II$^+$.

After these cells have been cultured in vitro, or following physiological stimulation with antigen, expression of the MHC II molecules increases and CD 25, B 7, CD 40 and ICAM 1 are also expressed.

The dendritic cells (abbreviated DC) are antigen-presenting cells which are able to induce activation of T cells with a high degree of efficiency. They are highly specialized and optimally equipped for their task, since dendritic cells express molecules which are required for presenting antigen (MHCI and MHCII) in large quantity. In addition to this, these cells express the constitutively co-stimulatory molecules CD80 and CD86 on their surface. These molecules are in turn essential for activating the T cells. Important adhesion molecules, which guarantee intimate contact with the target cell, are also present on the surface of the dendritic cells.

Two maturation stages can be distinguished in dendritic cells. These cells of the Langerhans' type (abbreviated LC) are distributed throughout the body in non-lymphatic organs. Their task is to take up antigen and process it. While there are no specific markers for these cells, they express the following markers: CD 1a, CD 11b, CD 33, HLA-DR and CD 80. More specific detection can be achieved by means of electron microscopy. The so-called Birbeck granules, which are only possessed by Langerhans' cells, can be detected electronmicroscopically.

In the body, the Langerhans' cells migrate, after contact with antigen, from the periphery of the body into the lymphatic organs by way of the lymphatic system. During this journey, they differentiate into mature immunostimulatory dendritic cells which no longer take up any antigen but on the other hand induce powerful T cell responses.

It is possible, therefore, to distinguish between Langerhans' cells and mature dendritic cells (abbreviated DC). Typically, these DC cells exhibit a decrease in the expression of CD 1a and an increasing expression of CD 4, CD 25 and CD 80.

The dendritic cells can be used, for example, in reinforcing an anti-infection therapy. The antigen-presenting dendritic cells are of particular importance in viral and bacterial infections, and the addition of these cells in connection with the appropriate infections can have advantageous effects on the patient, in particular in severe cases. Another possible area of employment is vaccination, because this would reinforce the immune response of the body.

The cells which can be prepared by means of the process according to the invention are of particular importance because of their powerful antigen presentation. The dendritic cells which can be obtained according to the invention can be loaded with specific antigens for different vaccination therapies in order, in this way, to induce a specific T cell response.

Furthermore, the use of the dendritic cells which can be obtained in accordance with the invention is of great importance in the immunotherapy of malignant and infectious diseases. Thus, the dendritic cells which can be prepared in accordance with the invention can be isolated individually from any patient and, for example in adoptive tumour immunotherapy, be loaded with specific tumour antigens and retransfused into the patient, thereby inducing a specific immune response against the tumour.

In the therapy of infectious diseases, the dendritic cells which can be obtained in accordance with the invention can be employed for reinforcing an immunization reaction in immunosuppressed patients, for example in association with vaccinating against hepatitis and, where appropriate, in association with vaccinating against HIV viruses. The dendritic cells which can be obtained in accordance with the invention can also be employed advantageously in association with other vaccinations.

The control of different bacterial or viral infections is a particular problem in patients who have to undergo chemotherapy as the result of a tumour disease, because the immune response of the patient is drastically reduced by the chemotherapy. It is necessary, therefore, to improve the immune response in precisely these cases. In addition to this, dendritic cells can, in particular, be used in the therapy of minimally residual diseases. Here, tumour-specific antigens are presented by the dendritic cells which then evoke a T cell-specific (cytotoxic) reaction.

The procedure for carrying out the process according to the invention for the ex-vivo expansion of dendritic cells can be as follows: heparinized blood samples are obtained from the patients. In the process according to the invention, cells which have been isolated from blood can be used as the starting material. This represents a substantial advantage as compared with the process disclosed in EPA 92.400879.0, in which process the cells have to be derived from the bone marrow or umbilical cord blood. Preferably, mononuclear cells (MNC) can be isolated from the apheresis product using suitable separation techniques, in particular by density gradient centrifugation through FICOLL (a nuetral, highly branched, hydrophilic polymer of sucrose (Pharmacia, Germany).

In an alternative embodiment, the CD 34$^+$ cells can be obtained from a leucapheresate in which the mononuclear cells are already enriched.

The mononuclear cells can be enriched by means of density centrifugation both when the CD 34+ cells are isolated directly from the blood and when the CD 34+ cells have been isolated from a leucapheresate. While a density centrifugation is preferred, it is not absolutely necessary.

If the CD 34+ cells have been isolated directly from the blood (heparinized blood samples), lysis of the erythrocytes could suffice and this could be followed, at the next purification step, by an affinity column or another enrichment step.

If the CD 34+ cells are isolated directly from the leucapheresate, these cells can be added to an affinity column (for example CellPro) after only one washing and without FICOLL separation. Enrichment using FICOLL gradients can be omitted, in particular, when relatively large quantities of CD 34+ cells are already present, as can be the case, for example, in association with high-dose chemotherapy.

In a preferred embodiment of the present invention, the process for preparing dendritic cells can comprise the following steps:

a) In order to mobilise the stem cells, the patient is treated with G-CSF, with customary concentrations of G-CSF being administered;

b) after a suitable period of time, approximately 50 to 100 ml of blood are removed;

c) a Ficoll separation step can be carried out if the content of CD 34+ cells is low;

d) the erythrocytes can be lysed;

e) a CD 34-isolation procedure can be carried out, which procedure, in a particularly preferred embodiment, is an affinity chromatography step;

f) Langerhans' cells and dendritic cells can be differentiated by adding growth factors/cytokines which are described below.

The Langerhans' cells/dendritic cells which are obtained in this way can be subjected to further treatment, depending on the purpose, and then reintroduced into the patient. A leucapheresis for the purpose of enriching the stem cells is particularly helpful when relatively large quantities of Langerhans' cells/dendritic cells are required.

The mononuclear cells are subjected to further treatment in order to enrich those cells which possess the CD 34 surface antigen. Berenson et al. described the CD 34 antigen in the publication "Engraftment After Infusion of CD 34+ Marrow Cells in Patients With Breast Cancer or Neuroblastoma" (Blood, Vol. 77, No. 8 (1991) pp. 1717–1722). These cells can be enriched by incubating the cells with a monoclonal antibody which is specific for the CD 34 antigen, with the antibody preferably being biotinylated. Monoclonal antibodies of this kind can be obtained commercially, for example from Dianova, Coulter, CellPro or Becton Dickinson. The cells which have been treated with the monoclonal antibody are loaded on to immunoaffinity columns, preferably avidin immunoaffinity columns, where the avidin binds the monoclonal antibodies and consequently also the CD 34+ cells which are bound to the antibodies. The absorbed cells, possessing the CD 34 surface antigen, are removed from the immunoaffinity column and introduced into a suitable medium.

Likewise, the monoclonal antibodies which are specific for the CD 34 antigen could be bound directly to a solid phase (for example small beads, etc.) in order to fix the CD 34+ cells and remove them from the mixture.

In addition, it is possible to enrich the CD 34+ cells using a fluorescence-activated cell sorter, which can be obtained commercially, for example from Becton Dickinson. In this procedure, mobilized peripheral blood progenitor cells are reacted with an anti-CD 34 antibody which possesses a fluorochrome label. Using the fluorescence-activated cell sorter, it is possible to separate the cells in order to obtain the CD 34+ cells. Highly purified cells can be obtained in this way. Another possibility would be to separate off the CD 34+ cells by using magnetic beads which can be obtained commercially from Dynal, Baxter, Milteny and other firms.

The enriched CD 34+ cells were then cultured in a suitable culture medium. An example of such a medium is supplemented RPMI 1640 medium which contains 10% foetal calf serum. The culture medium can also contain heparinized autologous plasma, for example at a concentration of approximately 1%. RPMI 1640 medium which is supplemented with 200 mM L-glutamine, 50 µM β-mercaptoethanol, 100 mM sodium pyruvate, 50 µg/ml streptomycin, 50 U/ml penicillin, MEM vitamins and 10% foetal calf serum is preferably used as the culture medium.

When the cells were expanded, they were grown in the presence of a combination of different growth factors. The following growth factors were used in this context:

"interleukin-1 (IL-1), described by Gery I. et al., Method Enzymol. 116, 456–467 (1985); Lachmann et al., Methods Enzymol. 116, 467–497 (1985); March et al., Nature 315, 641 (1985);

interleukin-3 (IL-3) described in EPA 138 133, Ihle et al., Methods Enzymol. 116, 540–552 (1985); Otsuka et al., J. Immunol. 140, 2288–2295 (1988);

interleukin-4 (IL-4), which can be obtained from Genzyme Corp.;

interleukin-6 (IL-6), described in Brakenhoff et al., J. Immunol. 139, 4116–4121 (1987), Brakenhoff et al., J. Immunol. 143, 1175–1182 (1989);

granulocyte macrophage colony stimulating factor (GM-CSF), which can be obtained from Genzyme Corp.;

erythropoietin (EPO), described by Jacobs et al., Nature 313, 806–810 (1985), Sasaki et al., Methods Enzymol. 147, 328–340 (1987);

stem cell factor (SCF), described in WO 91/05 797, Nocka et al., EMBO J. 9, 3287–3294 (1990), and interferon-γ (IFN-γ), described in EP 77 670, Gray et al., Nature 295, 503–508 (1982); Devos et al., Nucl. Acids Res. 10, 2487–2501 (1982); Yip et al., PNAS 79, 1820–1824 (1982) and Braude, Methods Enzymol. 119, 193–199 (1986)."

Figure 1:
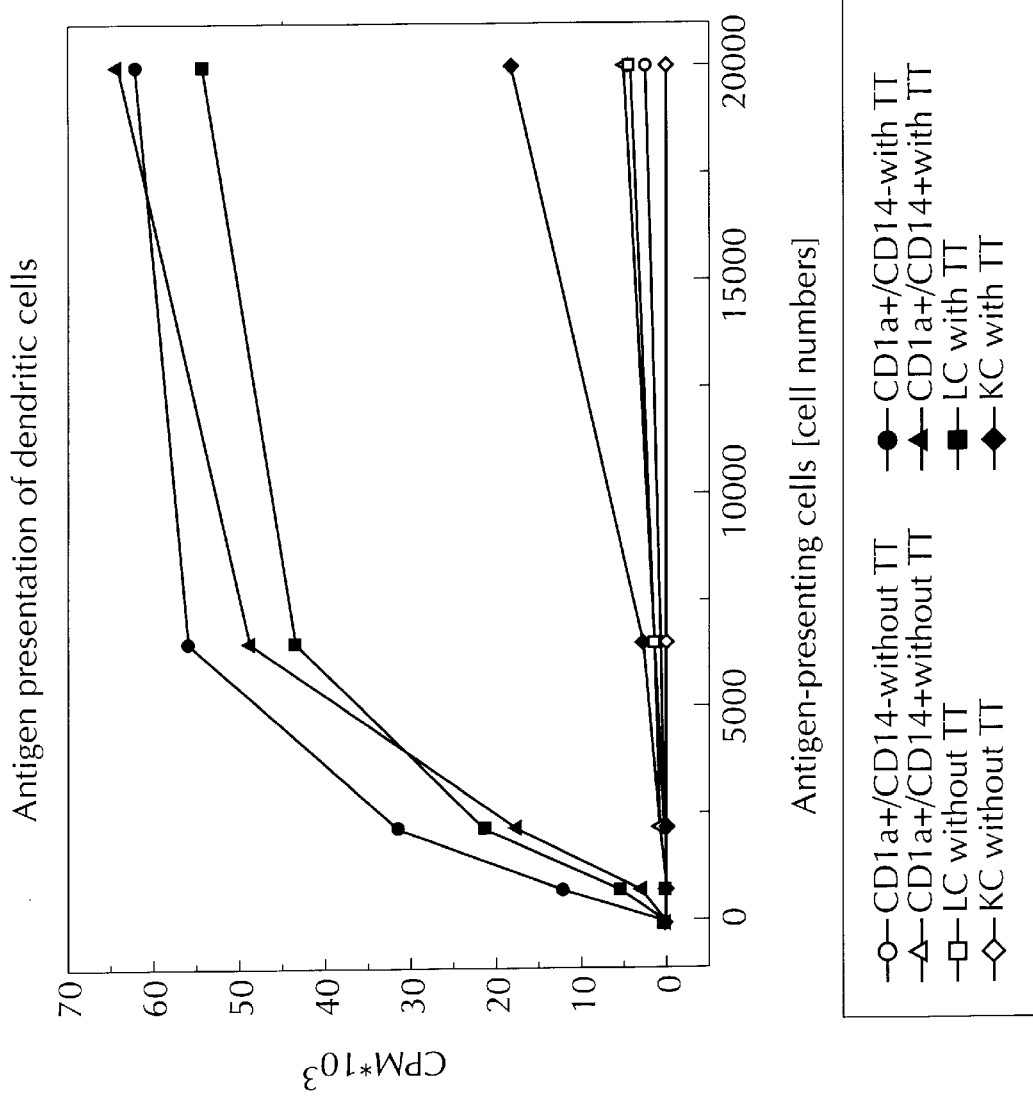
FIG. 1 depicts an assay of the ability of sorted and unsorted cells cultured in SE 126 plus IL-4 and GM-CSF to present antigen, tetanus toxin ("TT"). The assayed cells are: sorted CD 1a+/CD 14− cells (LC/DC) without or with TT depicted as open and closed circles; sorted CD 1a+/CD 14+ cells (LC/DC), without or with TT, depicted as open and closed triangles; unsorted cells from the LC/DC culture (LC), without or with TT, depicted as open and closed squares; unsorted cells cultured in medium containing only SE 126 (KC), without or with TT, depicted as open and closed diamonds.

It was found that the CD 34+ progenitor cells are expanded by a combination of the following growth factors: IL-1, IL-3, IL-6, EPO and SCF. When these five growth factors were used, from 1 to 5% dendritic cells, expressing the surface antigen CD 1a, were obtained. Such cells can also be identified electron-microscopically by detecting the so-called Birbeck granules. The yield of dendritic cells was markedly increased by adding TNF-α and GM-CSF.

The cells are cultured in the presence of the growth factors IL-1, IL-3, IL-6, EPO and SCF. It is important in this context that the cells are cultured in the presence of stem cell factor, with it being necessary for the medium to contain further cytokines and growth factors.

In a preferred embodiment, the cells are expanded in the presence of a combination of SCF, GM-CSF and TNF-α. Where appropriate, IL-4 (interleukin-4) can also be added (10–1000 ng/ml).

In a particularly preferred embodiment of the present invention, differentiation into dendritic cells is effected by using the cytokines IL-1β, IL-3, IL-6, SCF and EPO, which are employed together with the cytokines IL-4 and GM-CSF.

Culturing with the use of the abovementioned cytokines results, within the space of two to three weeks, in the maturation of a large number of cells which, from their morphology and their marker profile, are typical cells of the Langerhans' type. After about five weeks of culture in a medium which contains the seven cytokines mentioned, the cells assume the phenotype of mature dendritic cells. Loss of the Birbeck granules, a decrease in CD 1a expression and an increase in expression of the surface markers CD 4, CD 25 and CD 80 are typical for this maturation stage.

Within the scope of the present invention, a sequential addition of the cytokines is particularly preferred in order to be able to exert even better control over the differentiation of the cells. In this embodiment, the progenitor cells are initially, expanded for a period of from one to two weeks using cytokines IL-1β, IL-3, IL-6, SCF and EPO. After this time, proliferation has for the most part come to an end and the cells are transferred to a medium which only contains the cytokines IL-4 and GM-CSF. In this way, the cells can be halted, on their path of differentiation from the Langerhans' cells to the dendritic cells, at the stage of the Langerhans' cells, thereby bringing all the cells into roughly the same stage of differentiation. In this stage, the cells are particularly well suited for taking up and processing antigen.

If a uniform population of dendritic cells is necessary for the desired purpose, the dendritic cells can be enriched or purified by appropriate separation methods. One separation method could, for example, be that of reacting the cells with monoclonal antibodies which are directed against the CD 1a surface antigen. These cell/antibody complexes can then be separated either using immunoaffinity columns or using FACS (fluoresence-activated cell sorter).

The concentration of growth factors and cytokines which is used is within the normally used concentration which exhibits the highest efficiency in ex-vivo cultures. IL-1 can be used at a concentration which is in the range from 10 ng/ml to 1000 ng/ml; IL-3 is used at a concentration of from 1 U/ml up to 1000 U/ml; IL-4 is used at a concentration of from 1 U/ml up to 1000 U/ml; IL-6 is used at a concentration of from 10 U/ml up to 1000 U/ml. EPO can be present at a concentration which is in the range from 0.1 U/ml to 10 U/ml. SCF is used at a concentration of between 10 ng/ml and 1000 ng/ml, and IFN-γ can be used in a range of from 1 U/ml to 1000 U/ml. For GM-CSF, the concentrations which are employed are between 10 ng/ml and 1000 ng/ml, while for TNF-α they are between 10 U/ml and 1000 U/ml.

The preferred ranges for IL-1 are between 10 ng/ml and 150 ng/ml; for IL-3 they are between 50 U/ml and 150 U/ml; for IL-4 they are between 50 ng/ml and 200 ng/ml; for IL-6 they are between 50 U/ml and 150 U/ml; for EPO they are from 0.5 U/ml to 1.5 U/ml; for SCF they are from 10 ng/ml to 150 ng/ml; for GM-CSF they are from 50 ng/ml to 200 ng/ml; for TNF-α they are from 20 U/ml to 150 U/ml and for IFN-γ they are from 50 U/ml to 150 U/ml. It is within the ability of the average skilled person to determine the optimal efficacy of the growth factors and cytokines. There are internationally recognised standards for the abovementioned units.

According to a preferred embodiment of the present invention, the peripheral blood progenitor cells are obtained from patients who are suffering from cancer and who have been mobilized with conventional chemotherapy and colony-stimulating factors in order to combine a therapeutic treatment having a broad anti-tumour activity with simultaneous mobilization of peripheral blood progenitor cells. Mobilization can be obtained by treating the patients with a standard dose, consisting of VP 16 (500 mg/m$^2$), ifosfamide (4 g/m$^2$), cisplatin (50 mg/m$^2$) and, where appropriate, epirubicin (50 mg/m$^2$) (VIP (E) therapy), followed by the subcutaneous administration of G-CSF (obtainable from Amgen) at a dosage of 5 μg/kg/d for from 12 to 14 days. It is likewise possible to administer GM-CSF, which can be obtained commercially, for example, from Sandoz AG, Basle, under the trade mark "LEUKOMAX". The cancer patients can also be treated with a chemotherapy which consists of etoposide (VP 16), ifosfamide and cisplatin, followed by the combined sequential administration of recombinant human interleukin-3 (rhIL-3) and recombinant human granulocyte macrophage colony stimulating factor (rhGM-CSF).

It is particularly preferred to obtain the peripheral blood progenitor cells from the patient between day 10 and day 18 after the chemotherapy.

The present invention also comprises a culture medium for dendritic cells, containing a combination of IL-1, IL-3, IL-6, EPO and SCF and, where appropriate, interferon-γ and TNF-α. Another culture medium according to the invention contains a combination of SCF, GM-CSF and TNF-α.

A culture medium for dendritic cells which is particularly preferred within the scope of the present invention contains a combination of IL-1, IL-3, IL-4, IL-6, SCF, EPO and GM-CSF.

The culture media according to the invention are used for the in-vitro generation of Langerhans' cells and dendritic cells and contain the abovementioned combinations of growth factors and cytokines.

The biologically active compounds are used at the abovementioned concentrations. It is possible to prepare suitable receptacles which are provided with a culture medium for culturing peripheral blood progenitor cells, which medium contains the above-described combination of growth factors. Such receptacles can be blood banks, microtitre plates or tissue culture bottles. Such ready-to-use receptacles are also a subject-matter of the present invention.

Example 1

Mobilization of Peripheral Blood Progenitor Cells (PBPC)

As a part of their induction chemotherapy, 18 patients were treated with a conventional dose, consisting of VP 16 (500 mg/m$^2$), ifosfamide (4 g/m$^2$) and cisplatin (50 mg/m$^2$) (VIP), with the subsequent subcutaneous administration of recombinant human G-CSF (Amgen, Germany) at a dose of 5 μg/gk/d for from 10 to 14 days, in order to mobilise PBPCs. 12 patients having solid tumours and 6 patients having refractory non-Hodgkin lymphomas were included. The PBPCs were collected 10 to 12 days after the VIP chemotherapy. The peripheral blood progenitor cells were removed by leucapheresis using a so-called "small-volume chamber" (obtainable from Baxter) on day 10–12 after the VIP chemotherapy using the method described by Brugger et al. in J. Clin. Oncol. 20, pp. 1452–1459 (1992) and Brugger et al., British J. of Haematology 84, pp. 402–407 (1993).

Example 2

Culturing the PBPCs

Mononuclear cells (MNC) were isolated from the apheresis product by density gradient centrifugation through FICOLL-HYPAQUE (a standardized, sterile, ready-to-use medium comprising FICOLL) (1.007 g/ml) (obtainable from Pharmacia) and washed twice in phosphate-buffered saline (PBS).

Peripheral blood or bone marrow MNC cells were cultured as described in the state of the art (e.g. Kanz et al., Blood, 68, 991 (1986)). MNCs ($1 \times 10^5$) were immobilized in methyl cellulose (0.9%) and cultured in IMDM which was supplemented with 30% fetal calf serum (Paesel, Germany).

Example 3

Positive Selection of CD $34^+$ Cells From Cultured PBPCs Using Immunoaffinity Adsorption Columns The mononuclear cells (MNCs) were incubated with a biotinylated IgM anti-CD 34 monoclonal antibody, then washed and loaded on to an avidin immunoaffinity column. Adsorbed CD $34^+$ cells (target cell population) were removed from the avidin column and resuspended in RPMI 1640 medium (Seromed, Germany) which was supplemented with 3 mmol/L glutamine and $5 \times 10^{-5}$ mol/L β-mercaptoethanol (Sigma, Germany).

Example 4

Expansion of Enriched CD $34^+$ Cells in Suspension Culture

Enriched CD $34^+$ cells were cultured in flat-bottomed 96-well microtitre plates, at from 0.5 to $15 \times 10^3$ cells/mL, in RPMI 1640 medium supplemented with 10% foetal calf serum or different concentrations of autologous plasma. The above-described combination of growth factors was added immediately after seeding the CD $34^+$ cells in the microtitre plates (total volume 200 μL/well). Four-fold cultures of each one of the tested 36 growth factor combinations were prepared. The following haematopoietic growth factors and cytokines were used: IL-1, IL-3, IL-6, GM-CSF, EPO, TNF-α, IFN-γ and SCF. Growth factors such as IL-1, GM-CSF, IFN-γ and SCF were used at a concentration of 100 ng/ml, while the cytokines IL-3 and IL-6 were used at a concentration of 100 U/ml. Erythropoietin was used at a concentration of 2 U/ml and TNF-α at a concentration of 50 U/ml. The cells were incubated in 5% $CO_2$ at 37° C. for up to 28 days without any further addition of growth factors or medium. For the analysis, the contents of each well was resuspended and washed in RPMI 1640 in order to remove residual growth factors. The viability of the cells was assessed by trypan blue dye exclusion and by flow-cytometric staining with propidium iodide.

Example 5

Preparation of Dendritic Cells by an Ex-vivo Expansion of Peripheral CD$34^+$ Blood Progenitor Cells CD$34^+$ blood progenitor cells are cultured, at a cell density of from 0.5 to $3 \times 10^4$/ml, as described in Example 4, in RPMI 1640 medium over a period of at most 21 days in 25 ml cell culture bottles. The following growth factors and cytokines are added to the culture medium: IL-1β, IL-3, IL-6, SCF and erythropoietin at the concentrations mentioned in Example 4. In a second culture, TNF-α, GM-CSF and SCF are added to the medium in order to increase the yield of dendritic cells.

Samples are removed from the cultures weekly and analysed for immunophenotype by flow cytometry using a FACScan analyser (Becton Dickinson). The data are evaluated using the FACScan Lysis 2 software programme. For the two-colour labelling, the cells are washed in PBS containing 2% FCS and incubated, at 4° C. for 30 minutes, with a PE-conjugated antibody against CD33 together with in each case one of the following FITC-conjugated antibodies: anti-HLA-DR, anti-CD4, anti-CD1a (all from Becton Dickinson) and anti-CD25 (Dako). In addition to this, single labellings are carried out using antibodies against CD1b, CD1c and CD40 (Dyanova, Hamburg). This antibody labelling is carried out using the indirect method. In order to determine the percentage proportion of cells from the granulocytic and monocytic maturation cascade, the cells are additionally labelled with antibodies against CD15 (granulocytes) and CD14 (monocytes). Mouse isotype controls (IgG1-FITC and PE-conjugated IgG2a) are performed as negative controls. After the conclusion of the incubation, the cells are washed 2×and resuspended in 250 μl of PBS, without the addition of FCS, for the flow-cytometric analysis. In order to exclude dead cells, propidium iodide (PI) is added to each sample directly before the measurement and the PI-labelled dead cells are finally excluded from the analysis in an appropriate manner. 20,000 cells are analysed from each sample.

Results

After 12 days, the proportion of CD1a$^+$ cells in the culture containing TNF, GM-CSF and SCF is approximately 20%, with these cells also expressing HLA-DR molecules which likewise constitute a marker for dendritic cells. However, since it is only Langerhans' cells which express the surface marker CD1a to a high degree, the actual number of dendritic cells can be significantly higher still. In addition, CD1c is expressed in approximately 17% of cells and CD40 in approximately 45% of the cells. These molecules, too, are markers of dendritic cells.

While the medium which was supplemented with IL-1, IL-3, IL-6, SCF and erythropoietin gave rise to a larger number of clonogenic progenitor cells, the proportion of dendritic cells was significantly lower. CD1a$^+$ cells were found in approx. 4% of all the exvivo-expanded cells, while the proportion of CD1c-expressing cells was 3% and the proportion of CD40-expressing cells approx. 2%.

Example 6

The different culture conditions were compared with each other and the combination of growth factors which enabled the highest possible yields of Langerhans' cells and dendritic cells to be achieved was determined. Following an avidin immunoaffinity column step, 60% of the cells which were obtained exhibited the marker CD $34^+$. These cells were cultured in an RPMI medium containing 10% foetal calf serum. A mixture of the cytokines SCF, EPO, IL-1β, IL-3 and IL-6 was initially used as the growth factors. This mixture was given the abbreviated designation of SE 136. Use of this cocktail resulted in a high degree of expansion of the cells containing a cell nucleus and of the clonogenic progenitor cells.

A combination of either TNF-α/GM-CSF and SE 136 or of IL-4/GM-CSF and SE 136 was employed in order specifically to obtain differentiation into Langerhans' cells and dendritic cells. IL-4/GM-CSF was used as the control. The results of this experiment are given in Table 1, with the total yield of nucleate cells and cells possessing the CD 1a+ marker also being given, as is the surface structure of the cells.

Table 1 shows that addition of the cytokines IL-4/GM-CSF to the SE 136 cocktail resulted in the highest yield of cells possessing the CD 1a+ marker. This yield was up to 45% of all the nucleate cells. Depending on the purity of the affinity column, the yield can be increased to up to 65%. Using TNF-α/GM-CSF together with the SE 136 cocktail gave a lower yield of CD 1a+ cells. A higher proportion of the cells exhibited the CD 15 and CD 14 markers, which suggests that these culture conditions favor differentiation into granulocytes and monocytes.

While peripheral blood progenitor cells possessing the CD 34+ marker, which were grown using IL-4/GM-CSF, had a high percentage of CD 1a+ cells, they did not exhibit any expansion of the cell type. The example demonstrates, therefore, that the optimal yield of Langerhans' cells/dendritic cells is obtained by a combination of the growth factors IL-4/GM-CSF and the factors SCF, EPO, IL-1β, IL-3 and IL-6.

Table 1. Cell yield and phenotype of the peripheral blood progenitor cells which possess the CD 34+ marker and which were cultured in the presence of different cytokine combinations

|  | SE136[1] + +TNF-α/GM-CSF | SE136 + +IL-4/GM-CSF | IL-4/GM-CSF |
|---|---|---|---|
| Total yield of nucleate cells | | | |
| Day 0 | $1.0 \times 10^6$# | $1.0 \times 10^6$ | $1.0 \times 10^6$ |
| Day 7 | $6.4 \times 10^6$ | $9.0 \times 10^6$ | $1.1 \times 10^6$ |
| Day 10 | $2.5 \times 10^7$ | $2.9 \times 10^7$ | $1.7 \times 10^6$ |
| Day 15 | $8.2 \times 10^7$ | $4.9 \times 10^7$ | $3.4 \times 10^6$ |
| Day 20 | $1.1 \times 10^8$ | $5.2 \times 10^7$ | $4.7 \times 10^6$ |
| Day 24 | $1.0 \times 10^8$ | $5.2 \times 10^7$ | $6.8 \times 10^6$ |
| Day 27 | $1.0 \times 10^8$ | $3.7 \times 10^7$ | $5.0 \times 10^6$ |
| Yield of cells possessing the CD1a+ marker | | | |
| Day 7 | $1.4 \times 10^5$ | $3.7 \times 10^5$ | ND |
| Day 10 | $7.0 \times 10^5$ | $1.7 \times 10^6$ | ND |
| Day 15 | $2.2 \times 10^6$ | $5.2 \times 10^6$ | $7.5 \times 10^5$ |
| Day 20 | $2.7 \times 10^6$ | $9.3 \times 10^6$ | $1.4 \times 10^6$ |
| Day 24 | $2.2 \times 10^6$ | $1.2 \times 10^7$ | $1.9 \times 10^6$ |
| Day 27 | $2.0 \times 10^6$ | $1.7 \times 10^7$ | $2.5 \times 10^6$ |
| Surface markers[2] | | | |
| CD 1a | − | ++ | ++ |
| HLA-DR | ++ | +++ | +++ |
| B7-1 | − | + | + |
| CD 14 | ++ | + | + |
| CD 15 | +++ | ++ | ++ |

[1]SE 136 is a cytokine cocktail which contains SCF, EPO, IL-1β, IL-3 and IL-6.
[2]The antigen expression of the different cell populations was determined by flow cytometry on Day 20. The surface marker expression was assigned to the following allocation system, with the following classification based on the cell number being chosen: − = <5%; + = 5–25%; ++ = 25–50%; +++ = 50–100%; ND = not determined. # The results are based on six different experiments.

Example 7

The use of the dendritic cells according to the invention as antigen-presenting cells for inducing an immune response is explained in more detail with the help of the experiment, which is described in more detail below, for demonstrating the presentation of tetanus toxoid antigens. Other antigens, such as tumour antigens, can also be employed in this application in place of the tetanus toxoid.

a) Preparation of Prestimulated PBMCs 30 ml of blood were removed from a patient prior to beginning chemotherapy and administering G-CSF. The peripheral mononuclear cells (PBMCs) were isolated from this blood using FICOLL gradients. The PBMCs were then prestimulated with tetanus toxoid (obtainable from Behringwerke, Marburg) with the following procedure being used:

$1 \times 10^7$ PBMCs were cultured together with 1:80-diluted tetanus toxoid in a medium which contained 10% human serum. After seven days, 50 U/ml IL-2 were added to the cells, which were then cultured for a further four days. The cells which had been prestimulated in this way were initially frozen and then thawed once again two days before beginning the antigen presentation experiment. In this procedure, advantage is taken of the fact that the PBMCs already contain antigen-presenting cells which can take up tetanus toxoid and present it to the T cells which are likewise present. In this way, the tetanus toxoid-specific T cells are prestimulated and, in particular, also enriched by the addition of IL-2, since this cytokine supports the survival and growth of the T cells, while most of the other cell types die out.

b) Preparation of the Langerhans'/dendritic cells

Following chemotherapy and the administration of G-CSF, progenitor cells possessing the CD 34+ marker were isolated from the patient by means of leucapheresis and subsequent affinity chromatography. These cells were cultured using the preferred cytokine combination (SCF, EPO, IL-1β, IL-3, IL-6, IL-4 and GM-CSF) and differentiated into Langerhans' cells/dendritic cells using the process according to the invention.

In another batch, some CD 34+ cells were cultured in a medium which only contained the five expansion cytokines IL-1β, IL-3, IL-6, SCF and EPO.

On day 24, the cells were sorted using a FACS sorter from Becton Dickinson, with two subtypes of dendritic cells, namely CD 1a+/CD 14−, on the one hand, and CD 1a+/CD 14+, on the other hand, being isolated.

c) Antigen presentation experiment

The Langerhans' cells/dendritic cells described in b) were initially irradiated in order to be able to rule out further growth of these cells with certainty. These cells were then mixed with the prestimulated peripheral mononuclear cells which were obtained as described in a) and transferred to microtitre plates. In the control mixtures, the cells were cultured without any addition of tetanus toxoid; otherwise, tetanus toxoid was added at a dilution of 1:80.

The results of this experiment are depicted in FIG. 1. In the experiment, the following cell populations were tested for their ability to present antigen:

a) sorted CD 1a+/CD 14− cells (LC/DC), depicted as circles;
b) sorted CD 1a+/CD 14+ cells (LC/DC), depicted as triangles;
c) unsorted cells from the LC/DC culture (LC), depicted as squares;
d) unsorted cells from the culture which only contained expansion cytokines (KC), depicted as diamonds;
e) only PBMCs (control);
f) only antigen-presenting cells (a to d).

The mixtures were cultured for two days, after which $^3$H-thymidine was added and the mixtures were incubated for a further 18 hours. The cells were then harvested and washed, and the counts per minute (CPM) were determined. Since $^3$H-thymidine is incorporated into the cells during growth, the counts per minute are a measure of T cell proliferation and consequently a measure of the ability of the cells which were used to present antigen.

The following conclusions can be drawn from the experiment:

a) PBMCs alone do not exhibit any proliferation;
b) antigen-presenting cells (all the populations used) alone do not exhibit any proliferation (irradiation);
c) PBMCs+antigen-presenting cells do not exhibit any proliferation;
d) however, PBMCs+antigen-presenting cells+tetanus toxoid do exhibit strong proliferation depending on the cell type employed. The sorted LC-DC populations (CD 1a$^+$/CD 14$^-$ and CD 1a$^+$/CD 14$^+$) induced the strongest proliferation. The unsorted LC/DC population induces to a somewhat lesser extent. This can be attributed to the fact that this cell population also contains other cells which are not antigen-presenting. The KC population, i.e. the cells which only contained the expansion cytokines IL-1$\beta$, IL-3, Il-6, SCF and EPO, only induced a relatively weak proliferation.

The present experiment demonstrates that the Langerhans' cells/dendritic cells which were generated in vitro using the particularly preferred cytokine cocktail take up and present antigen in an outstanding manner and are able to induce very strong T cell responses. This property is less pronounced when IL-4 and GM-CSF are not present.

We claim:

1. A process for preparing dendritic cells, comprising
    a) culturing peripheral blood progenitor cells which express the CD 34 antigen in a cell growth medium comprising interleukin-1 (IL-1), interleukin-3 (IL-3), interleukin-6 (IL-6), erythropoietin (EPO) and stem cell growth factor (SCF),
    b) transferring the cultured peripheral blood progenitor cells into a medium which comprises interleukin-4 (IL-4) and granulocyte macrophage colony stimulating factor (GM-CSF).

2. The process according to claim 1, wherein the perpheral blood cells are isolated from a blood sample.

3. The process according to claim 1, wherein the cell growth medium in subsection (a) further comprises IL-4 and GM-CSF.

4. The process according to claim 2, comprising isolating said peripheral blood progenitor cells which express the CD 34 antigen from a heparinized blood sample by density gradient centrifugation.

5. The process according to claim 4, comprising isolating said peripheral blood progenitor cells which express the CD 34 antigen by density gradient centrifugation through a medium comprising a non-ionic polymer of sucrose.

6. The process according to claim 1, comprising contacting said peripheral blood progenitor cells with a monoclonal antibody which recognizes and binds to CD34 surface antigen and separating any peripheral blood progenitor cells which express the CD 34 antigen and bind to said monoclonal antibodies from said blood sample.

7. The process according to claim 6, comprising separating peripheral blood cells which bind the monoclonal antibody from said sample with an immunoaffinity column.

8. The process according to claim 7, wherein said monoclonal antibody is biotinylated.

9. The process according to claim 8, wherein said immunoaffinity column has avidin attached thereto.

10. The process according to claim 1, comprising obtaining said peripheral blood progenitor cells which express the CD 34 antigen from a cancer patient treated with a therapeutically useful amount of a chemotherapeutic agent selected from the group consisting of etoposide (VP 16) ifosfamide and cis platin.

11. The process according to claim 1, comprising obtaining said peripheral blood progenitor cells from a cancer patient treated with a therapeutically useful amount of a chemotherapeutic agent selected from the group consisting of etoposide (VP 16), ifosfamide and cisplatin, followed by a combined, consecutive treatment with a recombinant human interleukin-3 (rhIL-3), recombinant human granulocyte macrophage colony stimulating factor (rhGM-CSF) or recombinant human granulocyte colony stimulating factor (rhG-CSF).

12. The process according to claim 1, comprising obtaining said peripheral blood progenitor cells which express the CD 34 antigen from a leucapheresate.

13. The method of claim 1, wherein the peripheral blood progenitor cells which express the CD34 antigen in (a) are cultured in the growth medium for one to two weeks before the peripheral blood progenitor cells are transferred into the medium in (b).

14. The method of claim 1, wherein the peripheral blood progenitor cells which express the CD34 antigen in (a) are cultured in the growth medium for one to two weeks before the peripheral blood progenitor cells are transferred into the medium in (b) wherein the hematopoietic growth factors in the medium in (b) consists of interleukin-4 and granulocyte macrophage colony stimulating factor.

15. A method for inducing T-cell activation in a patient in need thereof comprising administering to said patient a therapeutically useful amount of dendritic cells produced by the process of claim 1.

16. A kit useful for preparing dendritic cells, comprising:
    (a) a receptacle for a culture of blood progenitor cells;
    (b) a first sample of a medium which comprises a hematopoietic growth factor combination comprising interleukin-1 (IL-1), interleukin-3 (IL-3), interleukin-6 (IL-6), erythropoietin (EPO) and stem cells growth factor (SCF) and does not contain interleukin-4 and granulocyte macrophage colony stimulating factor;
    (c) a second sample of a medium which comprises a hematopoietic growth factor combination comprising interleukin-4 and granulocyte macrophage colony stimulating factor; and
    (d) a container means for said receptacle and said first and second samples of media.

17. The kit of claim 16 wherein said first sample of medium comprises interleukin-1 at a concentration of between 10 ng/ml and 1000 ng/ml, interleukin-3 at a concentration of from 1 U/ml to 1000 U/ml, interleukin-6 at a concentration of from 10 U/ml to 1000 U/ml, erythropoietin at a concentration of between 0.1 U/ml and 10 U/ml, and stem cell factor at a concentration of from 10 ng/mg up to 1000 ng/ml.

18. A kit for preparing dendritic cells consisting of separate receptacles for each of (1) a hematopoietic growth factor combination consisting of interleukin-1, interleukin-3, interleukin-6, stem cell factor and erythropoietin, and (2) a hematopoietic growth factor combination consisting of interleukin-4 and granulocyte macrophage colony stimulating factor.

* * * * *